United States Patent
Haider et al.

(10) Patent No.: US 8,176,787 B2
(45) Date of Patent: May 15, 2012

(54) SYSTEMS AND METHODS FOR OPERATING A TWO-DIMENSIONAL TRANSDUCER ARRAY

(75) Inventors: Bruno Hans Haider, Ballston, NY (US); Robert Stephen Lewandowski, Amsterdam, NY (US); Robert Gideon Wodnicki, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 719 days.

(21) Appl. No.: 12/337,328

(22) Filed: Dec. 17, 2008

(65) Prior Publication Data
US 2010/0152587 A1    Jun. 17, 2010

(51) Int. Cl.
*G01N 9/24* (2006.01)
*A61B 8/14* (2006.01)

(52) U.S. Cl. .......................... 73/626; 600/459
(58) Field of Classification Search .................. 73/626, 73/624–625; 600/447, 459
See application file for complete search history.

(56) References Cited

U.S. PATENT DOCUMENTS

| | | | |
|---|---|---|---|
| 2,817,023 A | 12/1957 | Rice | |
| 4,371,805 A | 2/1983 | Diepers et al. | |
| 5,329,496 A | 7/1994 | Smith et al. | |
| 5,590,658 A | 1/1997 | Chiang et al. | |
| 5,622,177 A | 4/1997 | Breimesser et al. | |
| 5,690,114 A | 11/1997 | Chiang et al. | |
| 5,839,442 A | 11/1998 | Chiang et al. | |
| 5,911,692 A * | 6/1999 | Hussain et al. | 600/447 |
| 5,957,846 A | 9/1999 | Chiang et al. | |
| 5,964,709 A | 10/1999 | Chiang et al. | |
| 6,106,472 A | 8/2000 | Chiang et al. | |
| 6,238,346 B1 * | 5/2001 | Mason | 600/459 |
| 6,384,516 B1 | 5/2002 | Fraser | |
| 6,419,633 B1 * | 7/2002 | Robinson et al. | 600/443 |
| 6,552,964 B2 | 4/2003 | Chiang et al. | |
| 6,641,534 B2 | 11/2003 | Smith et al. | |
| 6,865,140 B2 | 3/2005 | Thomenius et al. | |
| 6,875,177 B2 | 4/2005 | Mochizuki | |
| 6,971,992 B2 * | 12/2005 | Cerofolini | 600/447 |
| 7,257,051 B2 | 8/2007 | Thomenius et al. | |
| 7,280,435 B2 | 10/2007 | Thomenius et al. | |
| 7,300,403 B2 | 11/2007 | Angelsen et al. | |
| 7,353,056 B2 | 4/2008 | Hazard et al. | |
| 7,775,979 B2 * | 8/2010 | Thomenius et al. | 600/437 |
| 2005/0057284 A1 | 3/2005 | Wodnicki | |
| 2005/0237858 A1 | 10/2005 | Thomenius et al. | |
| 2007/0016026 A1 | 1/2007 | Thomenius et al. | |
| 2008/0027320 A1 * | 1/2008 | Bolorforosh et al. | 600/439 |
| 2009/0099454 A1 * | 4/2009 | Yao et al. | 600/459 |

FOREIGN PATENT DOCUMENTS

EP    1768101    3/2007

* cited by examiner

*Primary Examiner* — J M Saint Surin
(74) *Attorney, Agent, or Firm* — Scott J. Asmus

(57) ABSTRACT

According to embodiments of the present technique, a system and a method for addressing transducers in a two-dimensional transducer array is disclosed. According to one aspect of the present technique, the transducers are arranged in rows and columns, and the columns are coupled to a shared transmit and receive circuitry while the rows are coupled to a row selection circuitry. In another embodiment, each transducer is coupled to a separate, dedicated transmit circuitry and the columns are coupled to a shared receive circuitry.

22 Claims, 8 Drawing Sheets

SYSTEMS AND METHODS FOR OPERATING A TWO-DIMENSIONAL TRANSDUCER ARRAY

BACKGROUND

The invention relates generally to two-dimensional transducer arrays. In particular, the invention relates to techniques for addressing individual transducer elements within a two-dimensional transducer array.

A medical ultrasound imaging system forms an image by transmitting an acoustic wave into a subject and receiving and processing the reflected acoustic waves. Typically, a plurality of ultrasonic transducers both send the transmitted wave and receive the reflected waves. Such scanning comprises a series of measurements in which the ultrasonic wave is transmitted, the system switches to receive mode after a short time interval, and the reflected ultrasonic wave is received, beamformed, and processed for display.

The transducer elements are typically driven individually by an input voltage waveform. By implementing time delays and amplitude differences between the input waveforms, the individual transducer elements can be controlled to produce ultrasonic waves that combine to form a net ultrasonic wave that travels along a preferred vector direction and is focused in a selected area of the subject. Similarly, the reflected waves received by the transducers may be mathematically processed so that the net signal is indicative of the sound wave reflected from a single focal zone in the object. As with the transmission mode, this focused reception of the ultrasonic energy is achieved by imparting various time delays and gains to the signals received from the transducer elements and summing the resulting waveforms.

The quality or resolution of the image formed by the ultrasound imaging system is partly a function of the number of transducers in the array. Accordingly, to achieve high image quality, a large number of transducer elements is desirable. Furthermore, each transducer in the transducer array is coupled to the transmit and receive circuitry via an individual electrical connection. The technical difficulty and expense of fabricating a large number of electrical connections may limit the number of transducers that may be included in a typical transducer array. It may be advantageous, therefore, to provide improved techniques for addressing the transducers in a large two-dimensional transducer array.

BRIEF DESCRIPTION

According to embodiments of the present technique, a system and a method for addressing transducers in a two-dimensional array is disclosed. According to one aspect of the present technique, the transducers are arranged in rows and columns, and the columns are coupled to shared transmit and receive circuitry while the rows are coupled to row selection circuitry. In another embodiment, each transducer is coupled to separate, dedicated transmit circuitry and the columns are coupled to shared receive circuitry. In both embodiments, the number of individual electrical interconnects used to communicatively couple the transducers to the signal generating and receiving circuitry is reduced.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The techniques disclosed herein enable a transducer array to be fabricated without the use of individual dedicated processing electronics for each transducer. In accordance with embodiments disclosed herein, a two dimensional transducer array may be fabricated that uses a plurality of signal busses, each of which may be shared by several transducers. To enable activation of individual transducers, the transducers may be coupled to the signal bus through a switch that is activated by selection circuitry. By providing techniques of addressing transducers in an array that is less technically challenging and more economical, transducer arrays may be fabricated that are much larger compared to existing ultrasound technology, enabling new ultrasound techniques and devices with large two-dimensional transducer arrays.

Figure 1:
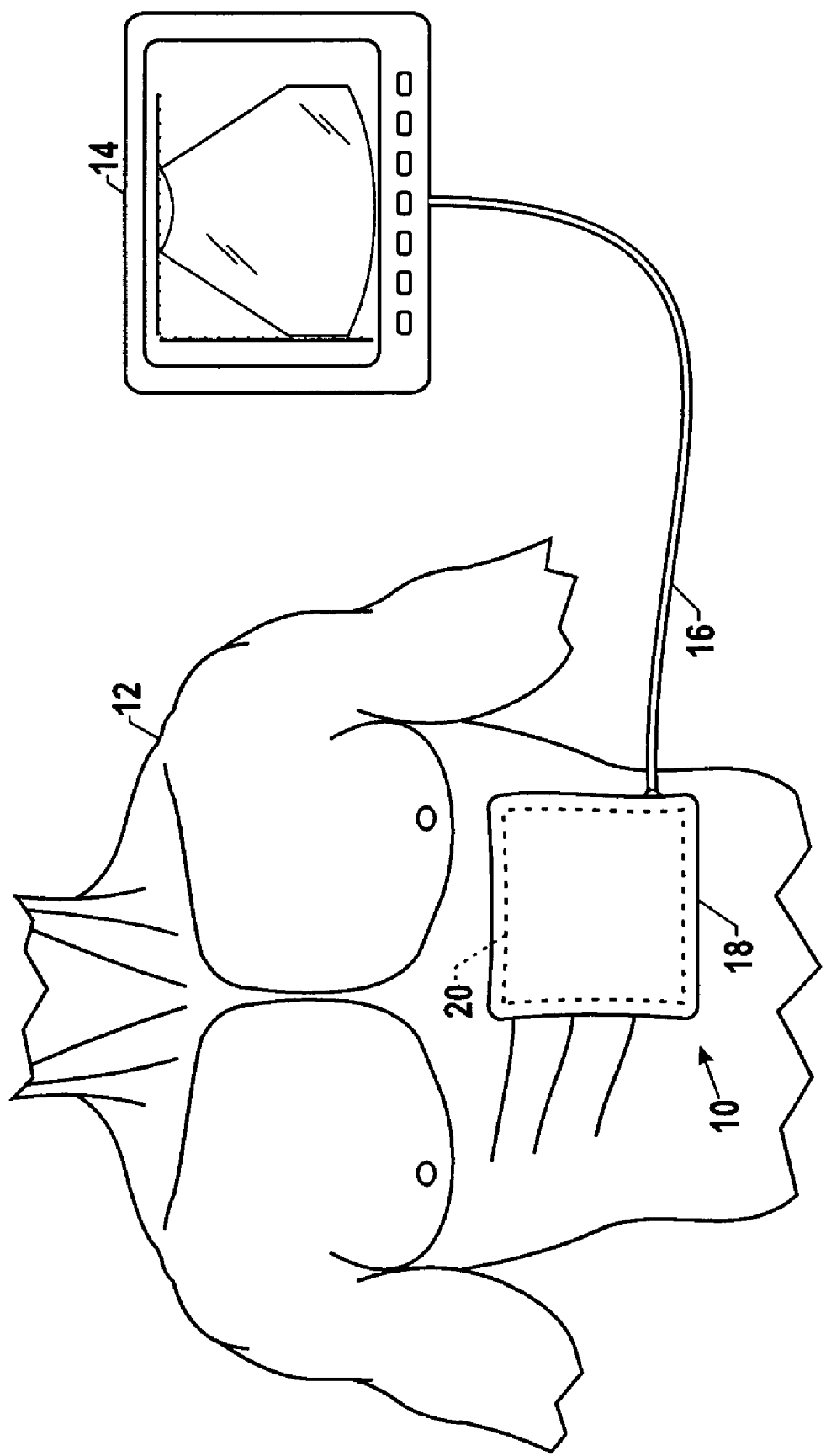
FIG. 1 is an exemplary ultrasound device that includes a two-dimensional transducer array with improved techniques for addressing individual transducers in accordance with aspects of the present invention.

FIG. 1 is an exemplary ultrasound device that includes a large two-dimensional transducer array with improved techniques for addressing the transducers in accordance with aspects of the present invention. As shown in FIG. 1, an improved ultrasound device 10 may be disposed adjacent to the tissue of a patient 12 and coupled to a monitor 14 through a communications cable 16. The monitor 14 allows the operator of the ultrasound device 10 to reconstruct and view the ultrasound image generated from signals received by the ultrasound device 10. Additionally, the monitor 14 may also provide control signals to the ultrasound device 10 through the communications cable 16. The ultrasound device 10 may include a housing 18, which serves to contain the transducer array 20 and enables the transducer array 20 to be brought into close proximity with the tissue of the patient 12. The housing 18 may include a thin flexible material that allows the ultrasound device 10 to conform to the tissue of the patient 12. In some embodiments, for example, the housing may include an elastomeric polymer such as a silicon-based polymer, polyvinylchloride, or a polyolefin such as polyethylene. The housing 18 may also include an adhesive backing for holding the ultrasound device 10 in place. Alternatively, the ultrasound device 10 may be held in place by an elastic band or straps.

The transducer array 20 is disposed inside the housing 18 and is held in close proximity to the patient 12 by the housing 18. The transducer array 20 may also be flexible to provide good contact with the tissue of the patient 12. In one embodiment, the transducer array 20 may be up to approximately 6" high and 6" wide and may include up to approximately 1,000,000 transducers arranged in a 1000 by 1000 matrix. The large number of transducers may enable automatic scanning, wherein the operator does not move the ultrasound device 10 in order to obtain ultrasound images for several image slices within the area of interest. Rather, several image slices may be obtained by electronically scanning the rows of the transducer array 20. To reduce the number of electrical interconnects used in the transducer array 20, the transducers may be coupled to several signal buses, or shared interconnects, as described below.

Figure 2:
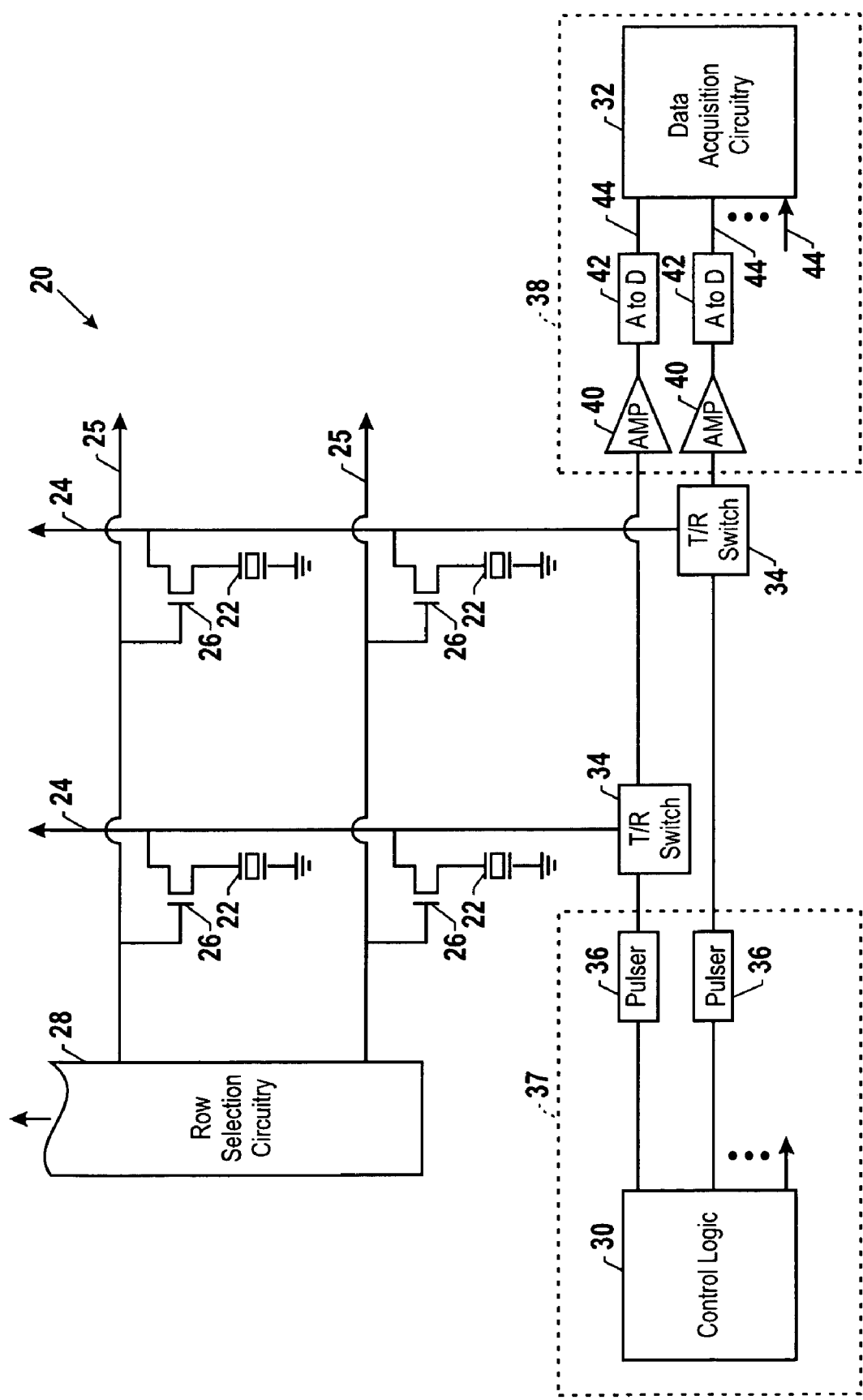
FIG. 2 is a block diagram of the two dimensional transducer array shown in FIG. 1 in accordance with aspects of the present invention.

FIG. 2 is a block diagram of the large two dimensional transducer array 20 shown in FIG. 1 in accordance with aspects of the present invention. The transducer array 20 includes transducers 22 arranged in a grid. For convenience, only two rows and two columns of the transducer array 20 are shown. It will be appreciated, however, that a transducer array in accordance with the present embodiments may include several rows and several columns for a total of up to several millions of transducers 22. The transducers 22 may be any type of ultrasound transducers such as capacitive micromachined ultrasound transducers (cMUTS) or piezoelectric transducers, for example.

Each of the transducers 22 in a single column may be coupled to a column bus 24, which is an electrical interconnect connecting each of the transducers 22 in the column to circuitry configured to send and receive ultrasound signals to and from the transducers 22. Each transducer 22 may be selectively coupled to the column bus 24 through a switch 26. The switch 26 may be any type of solid-state or other suitable switch, such as a field effect transistor or Micro Electro-Mechanical Systems (MEMS) switches and may be capable of passing high voltages (50-200V) in order to support the transmit voltage. The gates of each switch 26 may be coupled to a row bus 25, which is an electrical connection coupling each row of transducers to a row selection circuitry 28. The row selection circuitry 28 may selectively activate one or more rows of transducers 22 by sending a signal to the gates via the row bus 25, thereby coupling the selected row of transducers 22 to the column bus 24. By controlling the signals placed on the column bus and the row bus, the transducers 22 may be addressed individually or one or more rows at a time.

The column bus 24 couples each column of transducers 22 to transmit circuitry 37 and receive circuitry 38 through a transmit-and-receive (T/R) switch 34, which determines whether the column bus 24 is coupled to the transmit circuitry 37 or the receive circuitry 38. The transmit circuitry 37 may include control logic 30 configured to control the generation of the output voltage waveform that is sent to the transducers 22 via the column bus 24. To generate the output voltage waveform, the control logic 30 may send one or more control signals to a pulser 36 whose output is coupled to the column bus 24 and is configured to output a plurality predefined, discrete voltage levels. The signals from the control logic 30 cause the output voltage of the pulser 36 to step through the predefined voltage levels to create the desired output voltage waveform. In some embodiments, the pulser 36 may generate a square wave comprising three voltage levels: 0, +V, and −V. In other embodiments, the pulser 36 may output a waveform that includes several voltage levels and approximates a sinusoidal waveform. In yet other embodiments, the pulser 36 may generate an analog output waveform. Furthermore, the control logic 30 and or the pursers 36 may be configured to produce a different waveform for each column bus 24. For example, in some embodiments, the control logic 30 may produce a phase delay between the output waveforms of each column bus 24 to focus the overall ultrasound wave to a particular area of interest.

The receive circuitry 38 may include data acquisition circuitry 32, which receives data from the transducers 22 that represents the ultrasound wave reflected from the patient 12. The data acquisition circuitry 32 may then generate an ultrasound image from the data. The data acquisition circuitry 32 may also introduce phase delay and signal gain variations to the received data to focus the ultrasound image in a particular area of interest within the patient. The receive circuitry 38 may also include circuitry for converting the voltage waveform received from the transducers into a digital form suitable for the the data acquisition circuitry 32. In some embodiments, the receive circuitry 38 may include an amplifier 40 and an analog-to-digital converter (ADC) 42. The amplifier 40 may receive a voltage signal from the transducer 22 and may amplify the signal to a suitable level for the ADC 42. The ADC 42 then converts the signal received from the transducer 22 into a digital signal that may be sent to the data acquisition circuitry 32 for processing.

The T/R switch 34 controls the routing of signals to and from the column bus by controlling whether the column bus 24 is coupled to the transmit circuitry 37 or the receive circuitry 38. During the transmit stage, the T/R switch 34 couples the output signal from the pulser 36 to the column bus 24, and the output signal is thereby transmitted to the row of transducers 22 selected by the row selection circuitry 28. During the receive stage, the T/R switch 34 couples the column bus 24 to the amplifier 40. The signals received by the amplifier 40 from the transducers 22 are then digitized by the ADC 40 before being relayed to the data acquisition circuitry 32.

Using the addressing techniques described above, it is possible to selectively activate individual transducers 22 without using individual interconnects for each transducer 22. For a 100 by 100 array of transducers, for example, the number of interconnects may be reduced from 10,000 to 200. This may result in substantial savings in fabrication costs and allow the fabrication of much larger transducer arrays compared to typical ultrasound devices. In some embodiments, the ultrasound device may be configured to simultaneously address the entire transducer array 20 or a desired subset of the transducer array 20, such as an individual row or column.

The process of acquiring ultrasound data may include two stages: an output stage and a receive stage. During the output stage, the T/R switches 34 couple one or more of the column busses 24 to the output of the pursers 36, and the control logic 30 generates an output waveform that is then sent to the column busses 24. The row selection circuitry 28 then activates one or more rows of switches 26, thereby coupling the selected transducers 22 to the column busses 24. The selected transducers 22 then receive the output voltage waveform from the pursers 36 and transmit the resulting ultrasound waveform into the patient 12. In some embodiments, which will be described further below with regard to FIG. 3, the row selection circuitry 28 may scan the entire array 20 by sequentially activating each row of transducers 22 for a short period of time during the generation of the output waveform.

During the receive stage, the T/R switches 34 couple one or more of the column busses 24 to the input of the receive circuitry 38. The row selection circuitry then activates one or more rows of switches 26, thereby coupling the selected transducers 22 to the column busses 24. The selected transducers 22 then receive reflected ultrasound waveform from the patient 12 and transmit the resulting electrical signal to the receive circuitry 38, which digitizes and processes the signal to produce the ultrasound image. As in the transmit stage, the row selection circuitry 28 may be configured to scan the entire array 20 by sequentially activating each row of transducers 22 for a short period of time during the reception of the reflected ultrasound waveform. The row selection timing may be better understood with reference to FIGS. 3 and 4, which illustrate exemplary methods of addressing the transducers.

Figure 3:
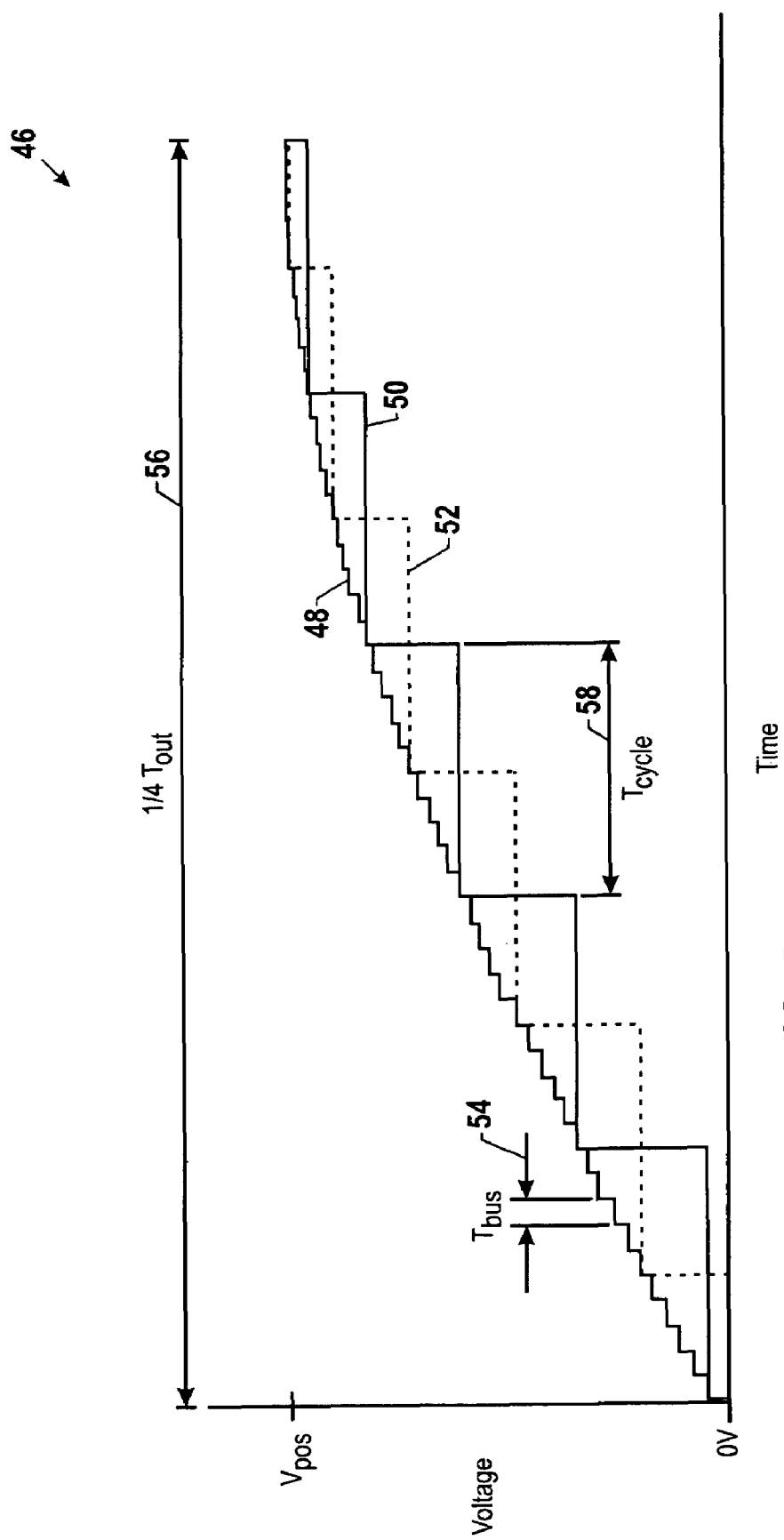
FIG. 3 is a graph of voltage versus time, illustrating the row selection timing and the corresponding voltage output of the transducer array shown in FIG. 2 in accordance with aspects of the present invention.

FIG. 3 is a graph of voltage versus time, illustrating the row selection timing and the corresponding voltage output of the transducer array shown in FIG. 2 in accordance with aspects of the present invention. For purposes of the present illustration, a 100 by 100 matrix of ultrasound transducers is assumed. Included in the graph 46 is a plot of the column bus output 48 generated by one of the pursers 36 shown in FIG. 2. As shown in FIG. 3, the column bus output 48 rises from zero Volts at time zero to a positive voltage, $V_{pos}$, after one quarter of the output period 56, ($T_{out}$). In some embodiments, $V_{pos}$ may equal approximately 100 Volts. Therefore, it will be appreciated that, in some embodiments, the switch 26 shown in FIG. 2 will be a high voltage switch. The column bus output 48 is a stepped output which approximates a sinusoidal waveform. In alternate embodiments, the column bus output 48 may be an analog signal or a square wave signal. Additionally, is should be noted that, for convenience, the graph 46 shows only one quarter of the column bus output 48. In the exemplary embodiment shown, the output frequency of the column bus signal may be approximately five Megahertz. Therefore, in the embodiment shown, the output period of the column bus signal may be approximately 200 nanoseconds, and the quarter period 56 (i.e. the time for the column bus output 48 to rise from zero to $V_{pos}$) is approximately 50 nanoseconds.

As discussed above, the rows of the transducer array 20 may be scanned, i.e. sequentially activated, during the output of the column bus signal 48. Each time a row is activated, the row is kept active for a period of time referred to herein as the "row activation interval," during which time the transducers in the activated row electrically charge or discharge according to the column bus voltage. The cycle time 58 ($T_{cycle}$) represents the amount of time it takes to scan the entire transducer array 20. In some embodiments, the entire transducer array 20 may be scanned every 10 nanoseconds, resulting in a row activation interval of 0.1 nanoseconds for a 100 row transducer array 22. In some embodiments, as shown in FIG. 3, the transducer array 20 may be scanned several times during the output of the column bus signal 48. As such, the transducers 22 may be activated several times as the column bus voltage varies in response to the output voltage waveform from the pursers 36. Each time the transducer 22 is activated, the transducer 22 charges or discharges in accordance with the column bus voltage that exists during the activation interval. Because the transducers are capacitive, the transducers 22 filter out the high frequency components introduced by the switching of the row selection circuitry 28 so that the output ultrasound waveform of the transducer 22 will approximate a smooth waveform.

The graph 46 shows the voltage applied to the transducers 22 of row one and row fifty as the one-hundred rows are sequentially activated. Trace 50 represents the voltage applied to row one, and trace 52 represents the voltage applied to row fifty. As shown by the graph 46, row one is switched on shortly after time zero, by which time the column bus signal 48 has stepped up to an initial voltage level. While row one remains activated, the transducers 22 of row one charge until they reach the voltage level of the column bus 24. Because all one hundred rows are activated during the cycle time 58, each row is activated for a time period equal to or less than the cycle time divided by the number of rows, in this case $T_{cycle}/100$.

However, after the transducers 22 are switched off, the output of the transducers 22 remain at the last voltage level reached during the activation period. After one passing of the cycle time 58 ($T_{cycle}$) row one is switched on again bringing row one up to the voltage level that exists on the column bus at that time. This process continues for each row of transducers 22 until the output waveform is finished transmitting. It is important to note that, despite the fact that each transducer row is activated at a slightly different time during the scan cycle, the phase difference of the output waveforms between different rows is very small. This can be better understood with reference to row fifty, represented by trace 52.

As shown by the graph 46, row fifty is activated at time $T_{cycle}/2$ and is activated again after each successive passing of the time interval $T_{cycle}$. As can be seen from the graph, although row one and row fifty are switched on at different times, very little phase delay exists between the two wave forms, because they are both sampling the output voltage waveform. It will be appreciated, however, that a small amount of phase delay between transducer rows may be introduced by the column bus signal 48, depending on the switching interval 54. Generally, the phase delay between the transducer output waveforms will be equal to or less than the switching interval 54 of the column bus ($T_{bus}$).

Figure 4:
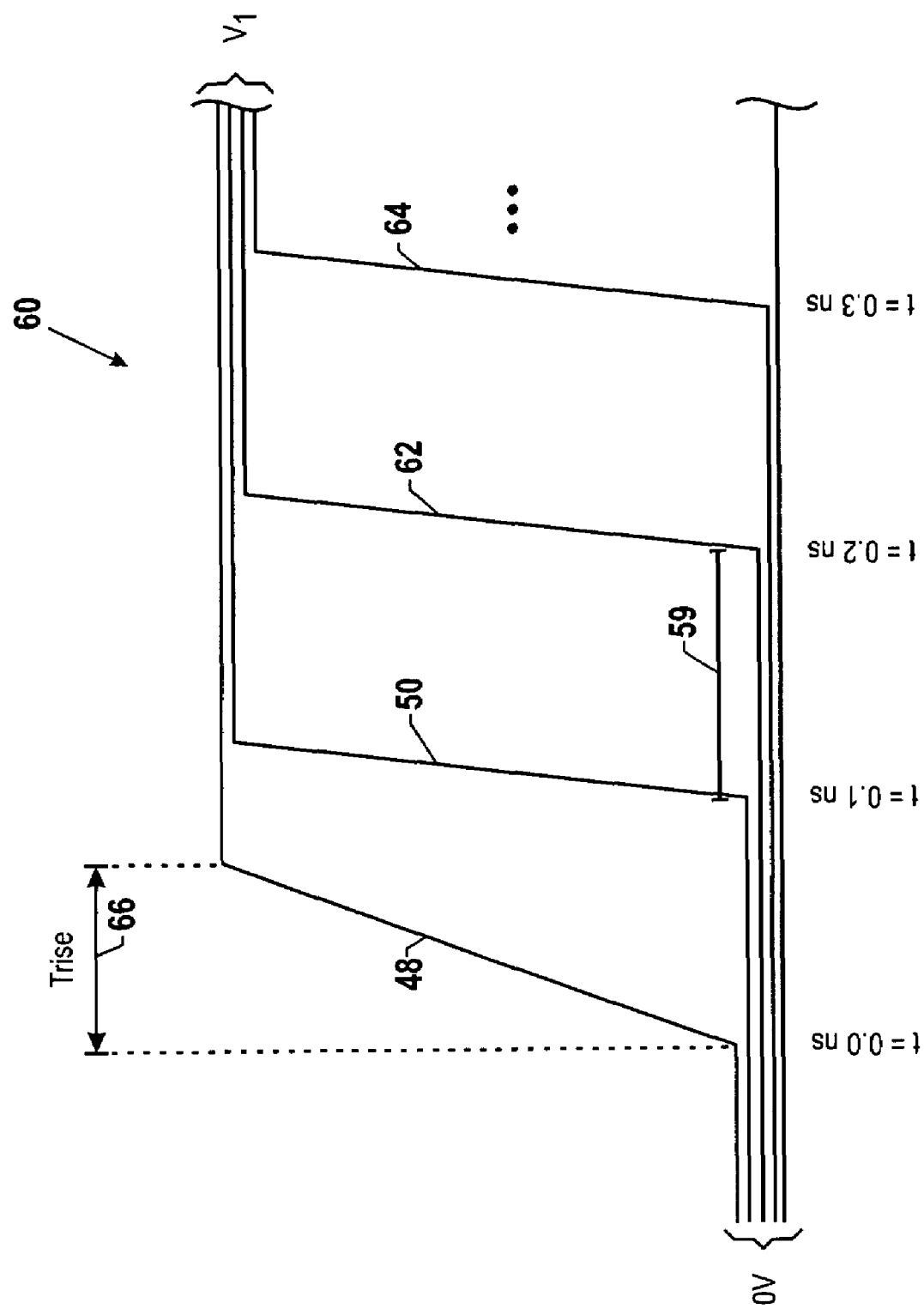
FIG. 4 is an expanded view of the graph of voltage versus time shown in FIG. 3 showing the row selection timing of the first three rows of transducers in accordance with aspects of the present invention.

FIG. 4 is an expanded view of the graph shown in FIG. 3 illustrating the row selection timing of the first three rows of transducers in accordance with aspects of the present invention. FIG. 4 shows the voltage across the transducers 22 during the selection of rows one, two, and three shortly after time zero. As shown in FIG. 4, the column bus signal 48 rises to a first voltage increment, $V_1$, shortly after time zero. Subsequently, row one represented by trace 50, row two represented by trace 62, and row three represented by trace 64 are switched on in succession. As stated above, the presently described embodiment assumes a transducer array 20 of one hundred rows and a cycle time 58 ($T_{cycle}$) of ten nanoseconds. Therefore, the row activation interval 59 for the presently described embodiment is approximately 0.1 nanoseconds. In other words, the row selection circuitry 28 sequentially activates successive transducer rows in increments of 0.1 nanoseconds. Accordingly, as shown in graph 60, row one is switched on at T=0.1 nanoseconds. At T=0.2 nanoseconds row one is switched off and row two is switched on. At T=0.3 nanoseconds row two is switched off and row three is switched on, etc. In some embodiments, the rise time 66 ($T_{rise}$) of the column bus signal 48 may be shorter than the row activation interval 59, thereby enabling the column bus signal 48 to stabilize at each incremental voltage level (e.g. voltage $V_1$) before the transducers rows are switched on.

The same process of sequentially selecting individual rows may be implemented during the receive stage, wherein the reflected ultrasound waveform is received by the transducers 22 and the transducers 22 generate a corresponding voltage signal that is delivered to the receive circuitry 38 via the column bus 24. To avoid aliasing, the sampling rate of the transducers 22 may be greater than twice the frequency of the received ultrasound waveform. Accordingly, for a five-Megahertz ultrasound waveform, the sampling rate of the transducers 22 may be greater than approximately 10 million samples per second (MSPS). Therefore, for a 100 row transducer array 20, the switching frequency of the row selection circuitry will be approximately 1 billion samples per second (GSPS). Additionally, because each column of transducers shares the same ADC 42, the sample rate of the ADC 42 will also be approximately 1 GSPS.

Figure 5:
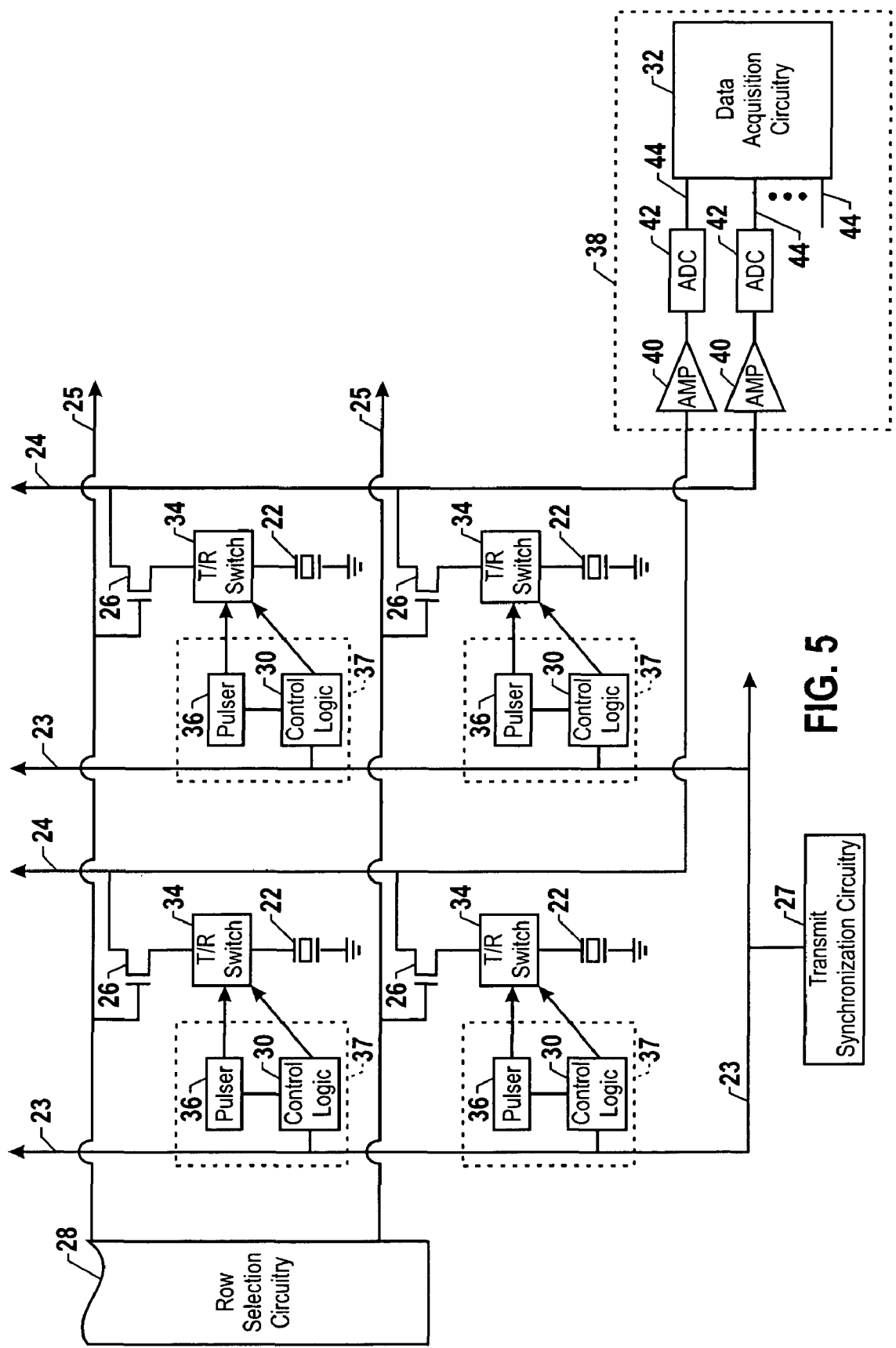
FIG. 5 illustrates an alternative embodiment of a two-dimensional transducer array in accordance with aspects of the present invention.

FIG. 5 illustrates an alternative embodiment of a large two-dimensional transducer array in accordance with aspects of the present invention. In the embodiment shown in FIG. 5, each transducer 22 in the array 20 is associated with a dedicated transmit pulser 36. Rather than acquiring a transmit signal from the column bus 24, each dedicated pulser 36 provides an output voltage waveform to the associated transducer 22 in response to drive signals from the associated control logic 30. The control logic 30 may be programmed to generate the full output waveform in response to a synchronization signal from a transmit synchronization circuitry 27, which may be communicatively coupled to the control logic 30 through a global control line 23. In this embodiment, the synchronization signal from the transmit synchronization circuitry 27 may trigger the control logic 30 simultaneously, causing the transducers 22 to transmit an output waveform simultaneously. Furthermore, by customizing the control logic 30 and/or the pulser 36 for each drive unit, the waveform of each transducer 22 may be more individualized.

In alternative embodiments, the transmit synchronization circuitry 27 may be eliminated. In this embodiment, initiation of the output ultrasound waveform would be handled by the row selection circuitry 28, which would send the synchronization signal to the control logic 30 through the row busses 25. As in the embodiment depicted, the synchronization signal may be sent to all of the rows sequentially or at substantially the same time. The control logic 30 may then initiate a routine that drives the pulser 36 to generate the output waveform.

The output of each transducer 22 may be coupled to the column bus 24, which routes the output signals from the transducer 22 to the receive circuitry 38. Furthermore, each transducer 22 may be coupled to the column bus 24 through a T/R switch 34, which controls the routing of signals to and from the transducer 22, and/or through the switch 26, which controls the selection of the transducer rows. In addition to driving the pulser 36, the control logic 30 may also control the T/R switch 34. For example, during the transmit stage, the control logic 30 may send a signal to the T/R switch that couples the transducer 22 to the output of the pulser 36. Moreover, during the transmit stage, all of the transducers 34 may be coupled to the respective pulser 36 simultaneously, because the transmit resources are not shared. During the receive stage, the control logic 30 may send a signal to the T/R switch 34 that couples the transducer 22 to the column bus 24. Depending on the speed of activation of the T/R switch 34, a low voltage MOSFET row select switch may be used instead. During the receive stage, only one row of transducers 22 may be coupled to the column bus 24 at a time. Thus the row selection circuitry 28 may sequentially couple the transducers 22 to the column bus 24 one row at a time during the reception of the reflected ultrasound waveform. As described above in relation to FIG. 3, the output of the transducer 22 may be sent to a receive circuitry 38 that may include an amplifier 40 and an ADC 42.

Figure 6:
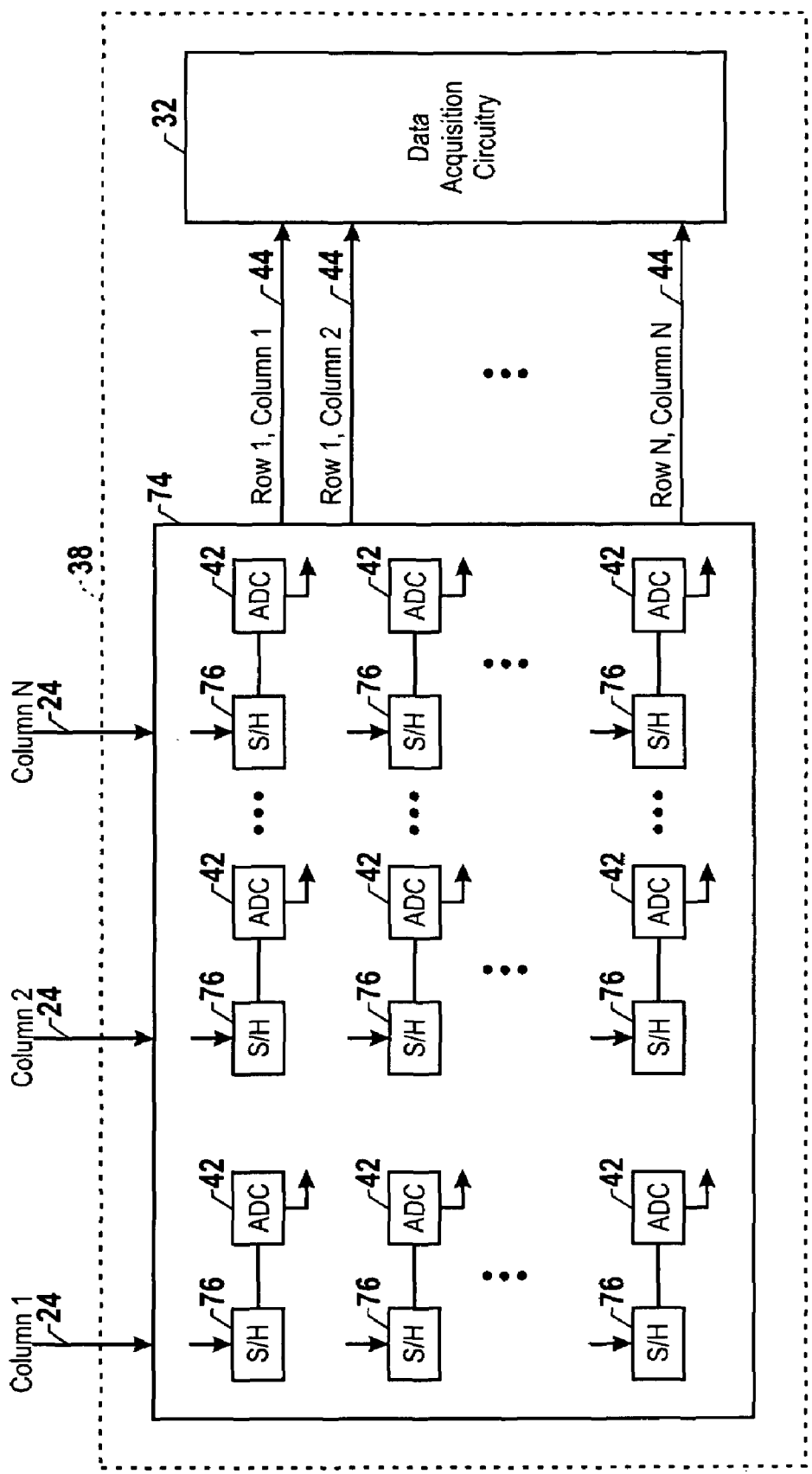
FIGS. 6-8 illustrate alternative embodiments of the receive circuitry used in the transducer array in accordance with aspects of the present invention.
Figure 7:
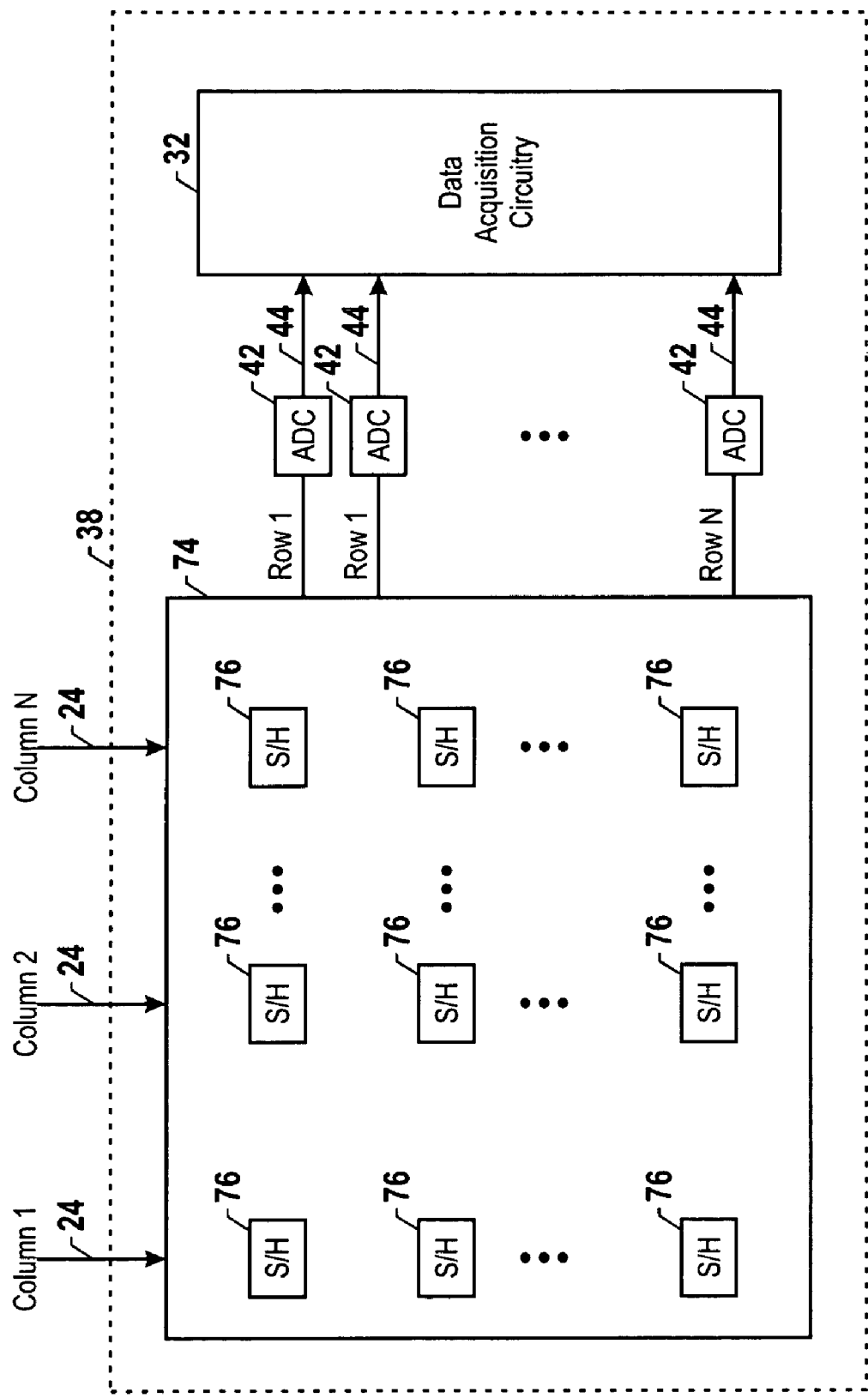

As shown in FIGS. 2 and 5, the receive circuitry 38 will, in some embodiments, be common for each column bus 24, and the receive circuitry 38 will be shared by the transducers 22 coupled to the column bus 24. Therefore, as described above, the sampling rate of the receive circuitry 38 may be the sampling rate of the transducers 22 multiplied by the number of rows in the transducer array 20. Assuming a transducer sampling rate of 10 MSPS and 100 rows of transducers 22, the sampling rate of the ADC 42 may be approximately 1 GSPS. Furthermore, the data received by the data acquisition circuitry 32 will be interlaced across several rows. In other embodiments, however, the receive circuitry 38 may be arranged to enable the use of ADCs 42 with reduced processing speeds and to provide some pre-processing of the received sample data. For example, the receive circuitry 38 shown in FIGS. 6 and 7 illustrate alternative embodiments of the receive circuitry 38, wherein the receive circuitry 38 may temporarily store the sample data in an analog memory device as it is received from the transducer array 20. In this way, the processing speed of the ADC(s) may be reduced, and/or the data may be pre-processed prior to being sent to the data acquisition circuitry 32, as will be explained further below.

FIG. 6 illustrates an alternative embodiment of the receive circuitry 38 in accordance with aspects of the present invention. As shown in FIG. 6, the receive circuitry 38 may include an array 74 of analog storage devices, such as sample-and-hold (S/H) amplifiers 76 and ADCs 42. In some embodiments, the analog storage devices may include an analog random access memory (RAM). The array 74 may include a pairing of one S/H amplifier 76 and one ADC 42 for each transducer 22 in the transducer array 20. As such, the S/H array 74 may be arranged in rows and columns corresponding with the respective rows and columns of the transducer array 20. Each S/H amplifier 76 may receive reflected waveform data from one of the transducers 22 of the transducer array 20 via the column bus 24. For example, the S/H amplifier 76 in column one of the array 74 may receive data from the transducers 22 in column one of the transducer array 20, the S/H amplifier 76 in column two of the array 74 receives data from the transducers 22 in column two of the transducer array 20, etc. The S/H amplifiers 76 may be coupled to their respective column bus 24 by any suitable means. For example, the column bus 24 may be multiplexed into the S/H amplifiers 76 of a particular column. For another example, the column bus 24 may feed into a pipeline such as a charge coupled device (CCD). For yet another example, the S/H amplifier 76 of a particular column may be arranged in series and coupled via shift registers, and the column bus 24 may be coupled to the input of the shift register column.

During the receive stage, the column busses 24 of the transducer array 20 are coupled to a particular row of transducers 22 in the transducer array 20, and the received data samples are stored in a corresponding row of the S/H amplifiers 76. After the row of S/H amplifiers 76 have acquired the new data sample, each S/H amplifier 76 may then send the data sample to the associated ADC 42 for converting the analog data into a digital signal. The digitized sample is then sent to the data acquisition circuitry 32 via the data lines 44. The above process is conducted sequentially row by row. It will be appreciated that there may be one data line 44 from the S/H array 74 to the data acquisition circuitry 32 for each transducer 22 in the transducer array 20. Additionally, because each S/H amplifier 76 is paired with a separate ADC 42, the processing rate of the ADC 42 may be equal to the sample rate of the transducers 22. For example, assuming a transducer sampling rate of 10 MSPS, the processing rate of the ADC 42 may also be approximately 10 MSPS regardless of the number of rows of transducers 22.

FIG. 7 illustrates another embodiment of the receive circuitry 38 in accordance with aspects of the present invention. Similar to the embodiment shown in FIG. 6, the embodiment shown in FIG. 7 may also include an array 74 of sample and hold (S/H) amplifiers 76 arranged in rows and columns corresponding with the respective rows and columns of the transducer array 20, and each S/H amplifier 76 may receive reflected waveform data from one of the transducers 22 of the transducer array 20 via the column bus 24. In the embodiment shown in FIG. 7, however, each row of S/H amplifiers 76 is paired with one ADC 42.

In this embodiment, after a row of transducers 76 receives a data sample, the row of S/H amplifiers 76 is then read out sequentially to the ADC 42. Each row of S/H amplifiers 76 may be coupled to their ADC 42 by any suitable means. For example, the row of S/H amplifiers 76 may be multiplexed into the ADC 42. For another example, the row of S/H amplifiers 76 may form a pipeline such as a CCD pipeline. For yet another example, the row of S/H amplifiers 76 may be arranged in series and coupled together via shift registers. In this way, the number of data lines 44 from the S/H amplifier array 74 to the data acquisition circuitry 32 may be reduced. Additionally, it will also be appreciated that the sample data collected in this way may be re-arranged from column interlaced to row interlaced before being sent to the data acquisition circuitry.

Figure 8:
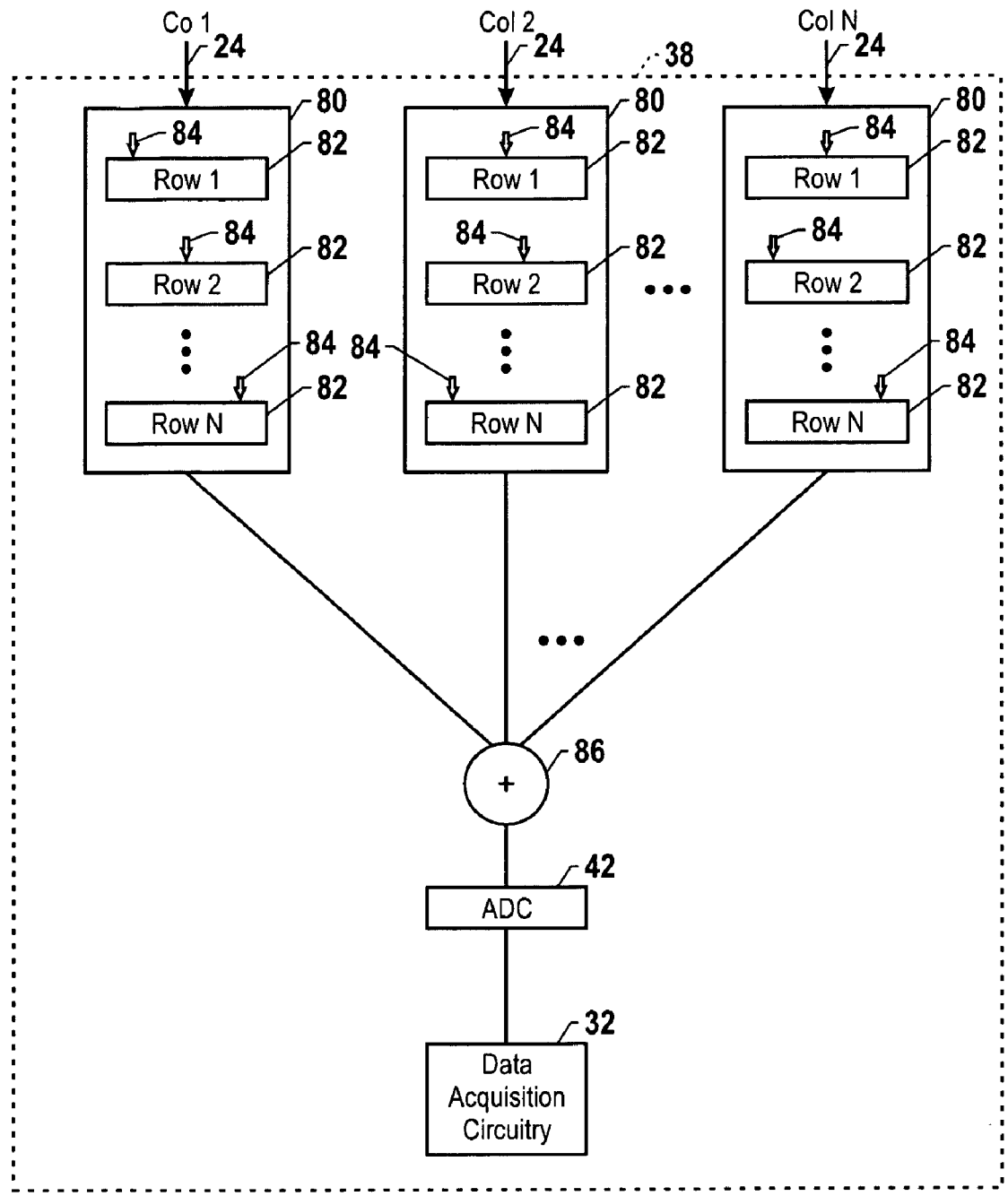

FIG. 8 illustrates yet another embodiment of the receive circuitry 38 in accordance with aspects of the present invention. In the embodiments shown herein, each column bus 24 of the transducer array 20 is coupled to an analog RAM bank 80 that includes an analog RAM 82 for each transducer 22 in the transducer array 20. Each RAM 82 includes a series of consecutive memory addresses configured to store the reflected waveform data received by a corresponding transducer 22 in the transducer array 20. As the rows of the transducer array 20 are sequentially activated by the row selection circuitry 28 during the receive stage, the data from the transducers 22 may be saved to the corresponding RAM 82. Accordingly, each RAM bank 80 may include circuitry for coupling each row in the transducer array 20 to the corresponding RAM 82 in the RAM bank 80. For example, in some embodiments, the RAM bank 80 may include multiplexing circuitry that sequentially couples the column bus 24 to the appropriate RAM 82 and is coordinated with the activation of the rows of the transducer array 20 by the row selection circuitry 28. In some embodiments, the multiplexing circuitry of the RAM bank 82 may be controlled, in part, by the row selection circuitry 28. After the reception of the reflected waveform is complete, the reflected waveform for each transducer 22 will be saved in an individual RAM 82. The waveform may then be read out of the RAM 82 and sent to the data acquisition circuitry 32, as described below.

In some embodiments, the receive circuitry 38 may include a summer 86 that sums the reflected waveforms one row at a time as they are read out of the analog RAM banks 80. For example, the RAM banks 80 may read out the first memory address of each RAM 82 in a single row of the RAM banks 80, then read out the second memory address of each RAM 82 in the same row of the RAM banks 80, etc. until the entire set of data stored in that row of RAM 82 has been read out and summed. As the data is summed, the output of the summer 86 is sent to the ADC 42, which digitizes the data and sends the data to the data acquisition circuitry 32. The data sent to the data acquisition circuitry 32 will, thus, be a composite waveform representative of one entire row of transducers 22. Each row is summed in succession until all of the data has been read out of each analog RAM bank 80. The technique described in reference to FIG. 8 enables the sample rate of the ADC 42 to be reduced because the processing of the output data may occur after the receiving of the full reflected waveform and is therefore not dependent on the sample rate of the transducers 22. Furthermore, by combining the output of each column into a summed signal, only one ADC 42 is used and the data acquisition circuitry 32 includes only one input for receiving the reflected data. This may reduce the cost and complexity of the receive circuitry 38 and the data acquisition circuitry 32.

Another advantage of the receive circuitry 38 shown in FIG. 8 is that it may also be used to implement beamforming, a process by which the ultrasound beam may be aimed in particular direction, i.e. the sensitivity of the ultrasound device 10 in a particular direction may be increased. To accomplish the beamforming two or more reflected waveforms may be shifted in phase (i.e. time shifted) and added together to create a composite waveform that represents a wave reflected from a particular direction. In the receive circuitry 38 of FIG. 8, a time delay may be introduced to the data stored in each RAM 82 by shifting the data across one or more memory addresses. In this way, when the data is later read out of the RAM 82 in sequential order, the shifting of the data will cause the data to be sent to the summer with a certain time delay compared to the other waveforms. Accordingly, the time delay introduced by the data shifting will depend on the sample rate of the transducers 22 and the number of memory addresses that the data is shifted.

In one embodiment, the data shifting is accomplished by setting a starting memory address as indicated by the pointer 84. The pointer 84 determines the location in the analog RAM 82 at which the first data sample of the reflected waveform is stored. Accordingly, the analog RAM 82 may include memory sufficient to hold the full reflected waveform plus the largest time delay. After all of the output data from the transducers 22 has been stored to the analog RAM 82, the desired delay will have been implemented. When the reflected waveform data is subsequently read out of each RAM 82, the read-out will start at the first memory address of each RAM 82.

Technical effects of the invention include the addressing of on or more transducers in a transducer array to generate an ultrasound wave and/or to receive a reflected ultrasound wave, wherein the transducers are coupled to shared electrical interconnects. Other technical effects include the preprocessing of received ultrasound data to enable reduced processing speeds for the analog-to-digital converters and the data acquisition circuitry.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An ultrasound imaging device, comprising:
   a two-dimensional transducer array including a plurality of transducers arranged in rows and columns;
   a plurality of column busses electrically coupled to the transducers, each column bus communicatively coupling the transducers of a single column to a respective transmit circuitry and a respective receive circuitry, the transmit circuitry configured to generate an output voltage signal for driving the transducers to produce an output ultrasound wave, the receive circuitry configured to receive an input voltage signal generated by the transducers in response to a reflected ultrasound wave;
   a plurality of switches, each switch coupled in series between one of the transducers and a respective column bus;
   a plurality of row busses electrically coupled to the switches, each row bus electrically coupling the switches in a single row to a row selection circuitry configured to selectively couple one or more of the rows of transducers to their respective column busses wherein the row selection circuitry sequentially couples the one or more rows for a duration equal to or less than a sampling period of the transducers divided by the number of rows selectively coupled to their respective column busses.

2. The ultrasound imaging device of claim 1, wherein the transmit circuitry comprises a pulser configured to output a plurality of predefined voltage levels.

3. The ultrasound imaging device of claim 1, wherein the switches are Micro Electro-Mechanical Systems switches.

4. The ultrasound imaging device of claim 1, wherein the receive circuitry comprises an analog-to-digital converter for each column bus.

5. The ultrasound imaging device of claim 1, wherein the receive circuitry comprises a plurality of analog storage devices, each of the analog storage devices coupleable to a corresponding transducer and configured to store a data sample of the input voltage signal generated by the corresponding transducer.

6. The ultrasound imaging device of claim 5, wherein the receive circuitry comprises a plurality of analog-to-digital converters equal to the number of analog storage devices and wherein each of the analog storage devices is coupled to one of the analog-to-digital converters.

7. The ultrasound imaging device of claim 1, wherein the receive circuitry comprises a plurality of analog storage devices, each of the analog storage devices coupleable to a corresponding transducer and comprising a plurality of memory elements configured to store a plurality of data samples corresponding with the input voltage signal generated by the corresponding transducer.

8. The ultrasound imaging device of claim 7, wherein the receive circuitry comprises a summer coupled to the analog storage devices and configured to sum the data samples from the analog storage devices to generate one or more composite waveforms; and
    an analog-to-digital converter coupled to the output of the summer and configured to convert the summed data to a digital signal.

9. An ultrasound imaging device, comprising:
    a two-dimensional transducer array that includes a plurality of transducers arranged in rows and columns;
    a plurality of column busses electrically coupled to the transducers, each column bus communicatively coupling the transducers of a single column to a respective receive circuitry configured to receive an input voltage signal generated by the transducers coupled to the column bus in response to a reflected ultrasound wave;
    a plurality of pulsers configured to generate an output voltage signal for driving the transducers to produce an output ultrasound wave, wherein each of the plurality of pulsers is coupled to a single transducer; and
    row selection circuitry configured to selectively couple the transducers to the column busses wherein the row selection circuitry sequentially couples the transducers for a duration equal to or less than a sampling period of the transducers divided by the number of transducers selectively coupled to their respective column busses.

10. The ultrasound imaging device of claim 9, wherein the row selection circuitry is configured to trigger the pulser to generate the output voltage signal.

11. The ultrasound imaging device of claim 9, comprising transmit synchronization circuitry configured to trigger the plurality of pulsers to generate the output voltage signal via a global control line.

12. The ultrasound imaging device of claim 9, wherein the output voltage signal approximates a sinusoidal waveform and includes a plurality of discrete voltage levels.

13. The ultrasound imaging device of claim 9, wherein the receive circuitry comprises a single analog-to-digital converter for each column bus.

14. The ultrasound imaging device of claim 9, wherein the receive circuitry comprises a plurality of analog storage devices, each of the analog storage devices coupleable to a corresponding transducer and configured to store a single data sample of the input voltage signal generated by the corresponding transducer.

15. The ultrasound imaging device of claim 14, wherein the receive circuitry comprises a plurality of analog-to-digital converters equal to the number of analog storage devices and wherein each of the analog storage devices is coupled one of the analog-to-digital converters.

16. The ultrasound imaging device of claim 9, wherein the receive circuitry comprises a plurality of analog storage devices, each of the analog storage devices coupleable to a corresponding transducer and comprising a plurality of memory locations configured to store a plurality of data samples corresponding with the input voltage signal generated by the corresponding transducer.

17. The ultrasound imaging device of claim 16, wherein the receive circuitry comprises a summer coupled to the analog storage devices and configured to sum the data samples from the analog storage devices to generate one or more composite waveforms; and
    an analog-to-digital converter coupled to the output of the summer and configured to convert the summed data to a digital signal.

18. A method of operating an ultrasound imaging device, comprising:
    receiving a reflected ultrasound waveform with a plurality of ultrasound transducers selectively coupleable to a signal bus and generating a received voltage waveform corresponding with the reflected ultrasound waveform;
    sequentially coupling each of the plurality of ultrasound transducers to the signal bus for a duration equal to or less than a sampling period of the transducers divided by the number of transducers coupled to the signal bus during the generation of the received voltage waveform.

19. The method of claim 18, comprising generating a plurality of output voltage waveforms and sending each one of the plurality of output voltage waveforms to one of the plurality of ultrasound transducers.

20. The method of claim 18, comprising generating an output voltage waveform and sending the output voltage waveform to the signal bus selectively couplable to a plurality of ultrasound transducers;
    sequentially coupling each of the plurality of ultrasound transducers to the signal bus during the generation of the output voltage waveform.

21. The method of claim 18, wherein generating the output voltage waveform comprises incrementing or decrementing an output voltage level of a pulser configured to provide a plurality of discrete output voltage levels.

22. The method of claim 18, wherein the sampling period of the transducers is approximately 100 nanoseconds.

\* \* \* \* \*